(12) United States Patent
Coufal

(10) Patent No.: US 7,041,822 B2
(45) Date of Patent: May 9, 2006

(54) METHOD FOR PURIFYING A MELAMINE MELT

(75) Inventor: Gerhard Coufal, Leonding (AT)

(73) Assignee: AMI - Agrolinz Melamine International GmbH, Linz (AU)

( * ) Notice: Subject to any disclaimer, the term of this patent is extended or adjusted under 35 U.S.C. 154(b) by 0 days.

(21) Appl. No.: 10/498,532

(22) PCT Filed: Dec. 10, 2002

(86) PCT No.: PCT/EP02/14007

§ 371 (c)(1),
(2), (4) Date: Dec. 28, 2004

(87) PCT Pub. No.: WO03/053943

PCT Pub. Date: Jul. 3, 2003

(65) Prior Publication Data

US 2005/0119483 A1    Jun. 2, 2005

(30) Foreign Application Priority Data

Dec. 12, 2001    (AT)  .............................. A 1949/2001

(51) Int. Cl.
*C07D 251/62*    (2006.01)
*C07D 251/60*    (2006.01)

(52) U.S. Cl. ....................................... 544/203; 544/201
(58) Field of Classification Search ................ 544/201, 544/203

See application file for complete search history.

(56) References Cited

U.S. PATENT DOCUMENTS

| 3,116,294 A | * | 12/1963 | Marullo et al. ............. 544/201 |
| 3,207,744 A | | 9/1965 | O'Hara et al. |
| 6,258,950 B1 | * | 7/2001 | van Wijck et al. .......... 544/200 |

FOREIGN PATENT DOCUMENTS

WO    WO 00/21940    4/2000

* cited by examiner

*Primary Examiner*—Venkataraman Balasubramanian
(74) *Attorney, Agent, or Firm*—The Webb Law Firm

(57) ABSTRACT

The invention relates to a method for producing pure melamine in a high-pressure method. According to said method, in the first stage, the melamine melt is brought into contact with hot $NH_3$ and $NH_3$ from the second stage and in the second step is brought into contact with cold $NH_3$ in such a way that it is cooled to a temperature, which is 1–30° C. above the pressure-dependent melting point of the melamine, before being optionally rested in a third stage and subsequently treated in various ways.

9 Claims, 1 Drawing Sheet

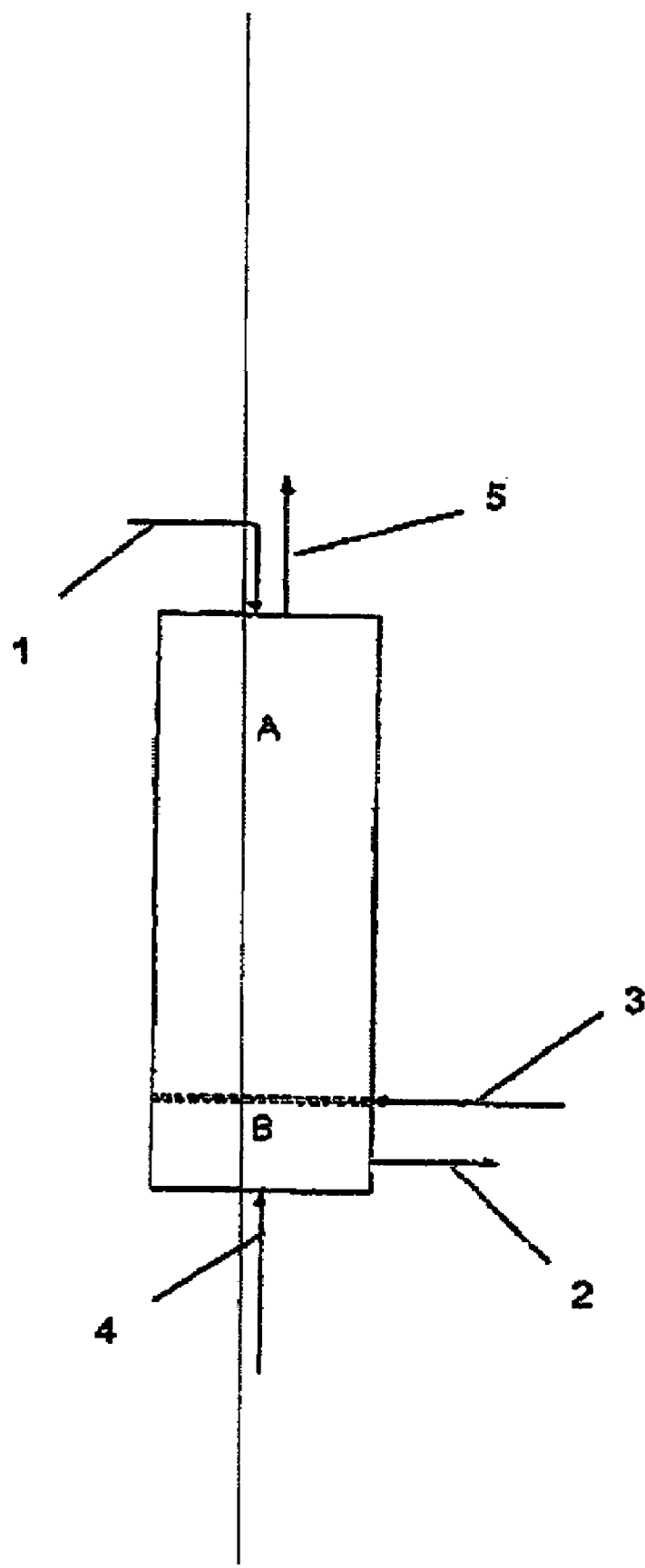

METHOD FOR PURIFYING A MELAMINE MELT

BACKGROUND OF THE INVENTION

1. Field of the Invention

The invention relates to the preparation of pure melamine by pyrolysis of urea in a high-pressure process and purification of the resulting melamine melt by divided stripping.

2. Description of the Prior Art

In high-pressure processes for preparing melamine, urea is reacted in an endothermic liquid-phase reaction to give melamine. In this reaction, 3 mol of $CO_2$ and 6 mol of $NH_3$ are formed per mole of melamine, and the liquid melamine contains, depending on pressure and temperature conditions in the reactor, additional varying amounts of dissolved $NH_3$ and $CO_2$ and also high molecular weight and low molecular weight by-products and unreacted urea.

It is known from U.S. Pat. No. 3,116,294 that the $CO_2$ can be removed from the crude melamine by countercurrent stripping of a crude melamine melt with gaseous $NH_3$. In WO 00/21940, it is stated that the stripping is advantageously carried out in a column which is filled with liquid melamine and not in a gas-filled column. Furthermore, it is possible to cool the melt in the bubble column to a temperature which is 5–20° C. above the melting point of melamine.

DETAILED DESCRIPTION OF THE INVENTION

Unexpectedly, a process which makes it possible to obtain a higher purity of the melamine by divided $NH_3$ introduction into the stripper has now been found.

The invention accordingly provides a process for preparing pure melamine in a high-pressure process by pyrolysis of urea, which is characterized in that the melamine melt formed is fed into a stripping unit in which the melamine melt is, in countercurrent,

- in a first stage brought into contact with hot fresh gaseous $NH_3$ and additionally with $NH_3$ from the second stage, with the temperature of the melt remaining the same or becoming higher,
- in a second stage brought into contact with cold gaseous $NH_3$ in such a way that it is cooled to a temperature which is 1–30° above the pressure-dependent melting point of melamine and, if desired,
- in a third stage left to rest for 10 minutes-10 hours, whereupon the melamine melt is worked up in any desired way.

To carry out the process of the invention, urea is reacted at a temperature of 325–450° C., preferably 350–425° C., and a pressure of 50–450 bar, preferably from 50 to 250 bar, to form liquid melamine and offgas. To avoid formation of by-products or, depending on the construction of the melamine reactor, to improve mixing in the reactor, excess $NH_3$ gas up to 10 mol of $NH_3$, preferably up to 2 mol of $NH_3$, per mole of urea is introduced into the reactor.

After the process of the invention, it is not necessary to feed the reaction mixture formed in the reactor into a separator and there separate the liquid phase, viz. the melamine melt, completely from the gaseous phase, viz. the offgases.

It is sufficient to take off the offgases at the top of the reactor and to pass the liquid phase which still contains amounts of dissolved offgases directly to the stripping unit.

The offgases taken off at the top of the reactor, which comprise gaseous $NH_3$, $CO_2$ and small amounts of gaseous melamine, are, if desired together with the offgases from further high-pressure parts of the melamine plant, which likewise comprise gaseous $NH_3$, $CO_2$ and small amounts of gaseous melamine, fed to a urea scrubber. In the urea scrubber, there is a urea melt which scrubs out the gaseous melamine present in the hot offgas and at the same time becomes hotter, while the offgas is freed of melamine and cooled. The preheated, melamine-containing urea melt is then fed into the melamine reactor and converted into melamine.

The melamine melt leaving the reactor additionally contains varying amounts of dissolved $NH_3$ and $CO_2$ and also relatively high molecular weight and low molecular weight by-products and unreacted urea. The $CO_2$ and the by-products and the unreacted urea should be removed as completely as possible from the melamine melt. According to the invention, this is achieved by divided stripping in a stripping unit in which the melamine melt is, in the first stage, stripped in countercurrent with hot fresh $NH_3$ and additionally with hot $NH_3$ from the second step, with the temperature of the melt remaining the same or being increased, and the melamine melt which has been prepurified in this way is, in the second stage, stripped with cold gaseous $NH_3$ in such a way that the melt is cooled to a temperature which is only just above the pressure-dependent melting point of melamine. Depending on the construction of the plant, this temperature is 1–30° C., preferably 1–20°, particularly preferably 1–10° C., above the pressure-dependent melting point of melamine.

The melamine melt is under an $NH_3$ pressure of 50–450 bar, preferably the reactor pressure. However, it is also possible to carry out stripping successfully at a pressure significantly below the reactor pressure. The temperature of the melamine melt entering the stripping unit is, in a preferred embodiment, about the same as the reactor temperature. However, it is also possible to increase or reduce the temperature. To carry out the stripping in the first stage, fresh ammonia having a temperature which is about the same as the temperature in the melt present in the first stage is introduced. However, it is also possible to feed in $NH_3$ having a somewhat higher temperature, so that the melt temperature in the first stage is increased overall.

At the same time as the fresh hot $NH_3$ is fed in, the now heated $NH_3$ obtained after passage through the second stage is also introduced into the first stage, so that the total amount of $NH_3$ used in the stripping unit at the high temperature necessary for optimal stripping is available for the stripping process in the first stage.

The inlet for the fresh hot $NH_3$ is present in any zone of the stripping unit in which the melamine melt which has been cooled in the second stage has reached approximately the entry temperature of the melamine melt into the first stage.

The amounts used, temperatures and particular structure of the stripping unit determines the position of the zone in which virtually no more cooling of the melamine melt takes place and in which the first stage commences and the fresh hot $NH_3$ is introduced. The fresh hot $NH_3$ gas can be introduced at one or more points.

The introduction of the cold $NH_3$ into the second stage is effected at the bottom of the stripping unit in an amount and at a temperature which cools the melamine melt to a temperature which is just above its respective melting point. However, it has to be ensured that the temperature does not drop below the melting point in the event of any fluctuation in operation, so that melamine crystallizes.

The temperature of the cold $NH_3$ is in the range 150–300° C., preferably 150–200° C., and the amount of cold $NH_3$ necessary is dependent on the entry temperature of the melamine melt, on the throughput, on the size and construction of the stripping unit, and can accordingly vary within a wide range.

During passage through the second stage, the cold $NH_3$ takes up the quantity of heat removed during cooling of the melamine melt and is in the process heated itself. In this second stage, relatively high molecular weight by-products, in particular, are removed.

In a further embodiment of the invention, there is room beneath the second stage for a third stage in which the melamine melt which has been brought to a temperature just above the melting point of melamine is left to rest under the prevailing $NH_3$ pressure. An additional aging effect can be achieved in this way.

The pure melamine melt obtained at the outlet of the second or third stage can be worked up further in any desired way and solidified, for example by depressurization of the melt, by solidification in a fluidized bed, by quenching with water, with liquid or gaseous ammonia, or by sublimation and subsequent desublimation from the gas phase.

The process of the invention is suitable for all types of gas-liquid columns. A wide variety of packing, for example perforated plates, sieve trays, valve trays or ordered packings such as Sulzer packing, can be used.

BRIEF DESCRIPTION OF THE DRAWINGS

FIG. 1 schematically shows a stripping unit in which A is the first stage of the stripping unit, B is the second stage of the stripping unit, 1 is the melamine melt entering the first stage, 2 is the melamine melt leaving the second stage, 3 is hot gaseous $NH_3$, 4 is cold $NH_3$ and 5 is outflowing $NH_3$.

Example 1 below shows that the divided addition according to the invention of $NH_3$ at different temperatures gives, at the same amount of $NH_3$ for stripping, melamine of higher purity than is obtained in the case of undivided $NH_3$ addition at constant temperature at the bottom of the reactor as in comparative example 1. Comparative example 2 shows that if the column has a temperature profile between inlet and outlet for the melamine melt, it is not possible to introduce the amount of "cold" $NH_3$ necessary for producing pure melamine, since the temperature of the melamine at the outlet of the stripping unit can then no longer be kept at the required temperature. Melamine having a lower quality still is obtained.

EXAMPLE 1

Divided $NH_3$ Addition 4 kg of melamine/hour having a temperature of 370° C. were introduced at the top into a column which had a length of 1 meter and a diameter of 8 cm, was packed with Sulzer packing and was under an $NH_3$ pressure of 180 bar. The melamine had a content of oxygen-containing components ($CO_2$, ammeline, ammelide, ureido-melamine and isocyanic acid) of 2.9% by weight. 0.43 kg of $NH_3$ at a temperature of 160° C. was introduced at the bottom of the column, and 2.9 kg/h of $NH_3$ at a temperature of 370° C. were introduced at the beginning of the temperature range of the melamine melt of 370° C.

At the bottom of the column, where the temperature is 340° C., melamine was obtained at a purity of 99.6% by weight and a content of oxygen-containing components of 0.21% by weight.

COMPARATIVE EXAMPLE 1

Undivided $NH_3$ Addition

As in example 1, 4 kg of melamine having a content of oxygen-containing components of 2.9% by weight and a temperature of 370° C. were introduced at the top of the column. However, the total amount of $NH_3$ of 3.33 kg/h was introduced at the bottom of the reactor and at a temperature of 370° C.

The purity of the melamine melt obtained at the bottom of the reactor was 99.0% by weight, and its content of oxygen-containing components was 0.22% by weight.

COMPARATIVE EXAMPLE 2

Undivided $NH_3$ Addition

As in example 1, 4 kg of melamine/having a content of oxygen-containing components of 2.9% by weight and a temperature of 370° C. were introduced at the top of the column. $NH_3$ having a temperature of 330° C. was introduced at the bottom of the stripping column until the temperature at the bottom of the column was 340° C.

The content of oxygen-containing components in the melamine melt obtained at the bottom of the reactor was 0.45% by weight, and the purity of the melamine was 99.2% by weight.

The invention claimed is:

1. A process for preparing pure melamine in a high-pressure process by pyrolysis of urea, wherein the melamine melt formed is fed into a stripping vessel having at least a first and a second separate gas inlet in which the melamine melt is, in countercurrent,
   in a first stage brought into contact with hot fresh gaseous $NH_3$ from the second stage, with the temperature of the melt remaining the same or becoming higher, whereby the gaseous $NH_3$ is injected at the first gas inlet into the first stage,
   in a second stage brought into contact with cold gaseous $NH_3$ in such a way that it is cooled to a temperature which is 1–30° C. above the pressure-dependent melting point of melamine, whereby the gaseous $NH_3$ is injected at the second gas inlet into the second stage,
   whereupon the melamine melt is worked up in any desired way.

2. The process as claimed in claim 1, wherein the melamine melt after the second stage is left to rest for 10 minutes-10 hours in a third stage.

3. The process as claimed in claim 1, wherein the melamine melt is in the second stage brought into contact with cold gaseous $NH_3$ in such a way that it is brought to a temperature which is 1–20° C. above the pressure-dependent melting point of melamine.

4. The process as claimed in claim 2, wherein the melamine melt is in the second stage brought into contact with cold gaseous $NH_3$ in such a way that it is brought to a temperature which is 1–20° C. above the pressure-dependent melting point of melamine.

5. The process as claimed in claim 1, wherein the melamine melt is in the second stage brought into contact with cold gaseous $NH_3$ in such a way that it is brought to a temperature which is 1–10° C. above the pressure-dependent melting point of melamine.

6. The process as claimed in claim 1, wherein the melamine melt comes directly from the reactor.

7. The process as claimed in claim 1, wherein the temperature of the melamine melt in the first stage is the same as the reactor temperature.

8. The process as claimed in claim 1, wherein the introduction of hot fresh gaseous $NH_3$ into the first stage is effected at a plurality of points.

9. The process as claimed in claim 1, wherein the temperature of the cold gaseous $NH_3$ introduced in the second stage is 150–300° C., preferably 150–200° C.

* * * * *

UNITED STATES PATENT AND TRADEMARK OFFICE
CERTIFICATE OF CORRECTION

PATENT NO. : 7,041,822 B2  Page 1 of 1
APPLICATION NO. : 10/498532
DATED : May 9, 2006
INVENTOR(S) : Coufal It is certified that error appears in the above-identified patent and that said Letters Patent is hereby corrected as shown below:

On Title Patent, See Item (73) Assignee, Line 2, "Linz (AU)" should read -- Linz (AT) --

Signed and Sealed this

Seventeenth Day of October, 2006

JON W. DUDAS
*Director of the United States Patent and Trademark Office*